United States Patent [19]

Kummer et al.

[11] 4,360,692
[45] Nov. 23, 1982

[54] PREPARATION OF FORMYLVALERATES

[75] Inventors: Rudolf Kummer, Frankenthal; Heinz-Walter Schneider, Ludwigshafen, both of Fed. Rep. of Germany

[73] Assignee: BASF Aktiengesellschaft, Fed. Rep. of Germany

[21] Appl. No.: 205,569

[22] Filed: Nov. 10, 1980

[30] Foreign Application Priority Data

Dec. 22, 1979 [DE] Fed. Rep. of Germany ....... 2951950

[51] Int. Cl.³ .............................................. C07C 67/38
[52] U.S. Cl. ..................................... 560/175; 560/206
[58] Field of Search ........................................ 560/175

[56] References Cited

U.S. PATENT DOCUMENTS

| 3,253,018 | 5/1966 | Zachry et al. | 560/175 |
| 3,743,674 | 7/1973 | Hohenschultz et al. | 562/522 |
| 3,778,466 | 12/1973 | Matsuda | 560/206 |
| 4,171,451 | 10/1979 | Kummer et al. | 560/206 |

OTHER PUBLICATIONS

Bull. Chem. Soc. of Japan, vol. 46, (1973), pp. 524–530.

Primary Examiner—Michael L. Shippen
Attorney, Agent, or Firm—Keil & Witherspoon

[57] ABSTRACT

An improved process for the preparation of alkyl formylvalerates, wherein butadiene or a butadiene-containing hydrocarbon mixture is reacted, in a first stage, with carbon monoxide and alkanols in the presence of cobalt carbonyl complexes and, per mole of butadiene, from 0.5 to 2 moles of tertiary nitrogen bases having a $pK_a$ of from 3 to 11, at from 80° to 150° C. and from 300 to 2,000 bar, and, in a second stage, the resulting alkyl pentenoate is reacted with carbon monoxide and hydrogen in the presence of cobalt carbonyl complexes at from 100° to 160° C. and from 100 to 300 bar, the improvement being that tertiary nitrogen bases, excess alkanols and any unconverted hydrocarbons are distilled off from the reaction mixture obtained in the first stage, with the proviso that the reaction mixture is treated, before or during the distillation, with gases containing molecular oxygen, and the residual reaction mixture containing alkyl pentenoate and cobalt catalyst is used in the second stage.

3 Claims, No Drawings

PREPARATION OF FORMYLVALERATES

The present invention relates to a process for the preparation of formylvalerates by reacting butadiene or butadiene-containing hydrocarbon mixtures with carbon monoxide and alkanols in the presence of tertiary nitrogen bases and cobalt carbonyl at from 80° to 150° C. under superatmospheric pressure and further reacting the pentenoate thus obtained with carbon monoxide and hydrogen at from 100° to 160° C. under superatmospheric pressure to give formylvalerates.

U.S. Pat. No. 3,253,018 discloses a process in which butadiene is first reacted with carbon monoxide and methanol in the presence of a rhodium catalyst to give methyl pentenoates, which are isolated from the reaction mixture. The methyl pentenoates thus obtained are then reacted in a second stage with carbon monoxide and hydrogen in the presence of a cobalt carbonyl catalyst to give methyl formylvalerate. A process of this type is expensive since a separate catalyst has to be used for each stage and the reaction mixture has to be worked up quantitatively after the first stage. A process for the preparation of methyl formylvalerate has also been disclosed in Bull. Chem. Soc. of Japan, Volume 46, 1973, pages 524 to 530. In this process butadiene, carbon monoxide and methanol are reacted in a first stage in the presence of cobalt carbonyl and isoquinoline at 130° C. and under 300 bar to give methyl pentenoate. The latter is distilld off from the reaction mixture thus obtained and in a further stage is subjected to hydroformylation with carbon monoxide and hydrogen in the presence of cobalt carbonyl at from 140° to 200° C. and from 100 to 250 bar, to give the formylvalerate. If the catalyst from the first stage is also to be used in the second stage, the tertiary nitrogen bases which are also present must be distilled off. However, during this distillation the catalyst decomposes with the precipitation of metallic cobalt and its effectiveness is considerably impaired.

It is therefore the object of the present invention to provide a process for the preparation of alkyl formylvalerates in which the cobalt carbonyl catalyst can be used in both stages without any intermediate separation being required.

This object is achieved by a process for the preparation of alkyl formylvalerates wherein butadiene or butadiene-containing hydrocarbon mixtures are reacted, in a first stage, with carbon monoxide and alkanols in the presence of cobalt carbonyl complexes and, per mole of butadiene, from 0.5 to 2 moles of tertiary nitrogen bases having a $pK_a$ of from 3 to 11, at from 80° to 150° C. and from 300 to 2,000 bar, and, in a second stage, the resulting alkyl pentenoates are reacted with carbon monoxide and hydrogen in the presence of cobalt carbonyl complexes at from 100° to 160° C. and from 100 to 300 bar, the tertiary nitrogen bases, excess alkanols and any unconverted hydrocarbons being distilled off from the reaction mixture obtained in the first stage, with the proviso that the said mixture is treated, before or during the distillation, with gases containing molecular oxygen, and that the residual reation mixture containing alkyl pentenoates and cobalt catalyst is used in the second stage.

The novel process has the advantage that only one catalyst need be used for the two process stages, that decomposition of the catalyst is prevented in a simple and effective manner and, finally, that the process can more simply be carried out continuously on an industrial scale.

The starting material used is either pure 1,3-butadiene or a butadiene-containing hydrocarbon mixture. Such mixtures of hydrocarbons contain, for example, saturated hydrocarbons of 3 to 5 carbon atoms and monounsaturated olefins of 3 to 5 carbon atoms, in addition to butadiene. The butadiene content should as a rule be more than 10 percent by weight. Industrially, C₄ cuts in particular are used as the starting mixture, these cuts being defined as all mixtures of predominantly unbranched $C_4$ hydrocabons containing more than 10% by weight of butadiene and more than 15% by weight of butenes. Depending on the origin of such mixtures, the individual components are usually present in the following proportions: from 40 to 60% by weight of butadiene, from 20 to 35% by weight of isobutene, from 10 to 5% by weight of 1-butene, from 5 to 15% by weight of 2-butene, from 1 to 10% by weight of butanes and from 0.1 to 3% by weight of butynes. C₄ cuts of this type are obtained, for example, from the dehydrogenation of butane or butene or as by-products from the production of ethylene by cracking naphtha or higher hydrocarbon cuts.

Preferred alkanols are $C_1$- to $C_4$-alkanols, eg. methanol, ethanol, propanol, butanol or isobutanol. Methanol is particularly preferred. The alkanols are preferably used in excess, advantageously in an amount of from 1.5 to 5 moles per mole of butadiene.

In the first stage, the reaction is carried out at from 80° to 150° C., especially from 100° to 140° C., and under from 300 to 2,000 bar, especially from 600 to 1,200 bar. As a rule, from 0.01 to 0.1 gram atom of cobalt in the form of cobalt carbonyl complexes is used per mole of butadiene.

Carbon monoxide is used in excess, advantageously, for example, in from 1.5 to 10 times the stoichiometrically required amount.

Preferred tertiary nitrogen bases having a $pK_a$ of from 3 to 11 are N-heterocyclic compounds such as pyridine ($pK_a$ 5.3), methylpyridines, eg. 3-picoline ($pK_a$ 6.0), isoquinoline ($pK_a$ 5.4) and trialkylamines, eg. trimethylamine ($pK_a$ 9.8) or triethylamine ($pK_a$ 11.0). Advantageously, the tertiary nitrogen bases used are those which are lower-boiling than the particular pentenoates to be prepared. Pyridine has become industrially particularly important. Advantageously, from 20 to 50 moles of tertiary nitrogen bases are employed per mole of cobalt carbonyl catalyst.

The cobalt carbonyl complexes used in the first stage can be formed in situ from cobalt salts, for example cobalt salts of fatty acids, such as the formate, acetate or butyrate. The catalyst is advantageously introduced in the form of cobalt carbonyl. In particular, it has proved suitable to introduce the cobalt carbonyl catalyst into the reaction mixture in the form of a solution in butadiene or a C₄ cut, the solution being obtained, for example, by first treating an aqueous cobalt salt solution with carbon monoxide and hydrogen, in excess, at from 50° to 200° C. and from 50 to 500 bar, in the presence of active carbon which is loaded with cobalt carbonyl. The cobalt salts preferably used are cobalt formate or cobalt acetate. The starting solution advantageously contains from 0.5 to 5% by weight of cobalt, calculated as the metal, in the form of the particular salt. In general, the gas mixture mentioned contains carbon monoxide and hydrogen in a ratio, by volume, of from 2:1 to 1:1; an approximately equimolecular weight has proved particularly suitable. The mixture of carbon monoxide and hydrogen is advantageously used in excess, for example in up to five times the stoichiometrically required amount. The active charcoal is loaded with cobalt carbonyl by passing an aqueous solution of a cobalt salt together with the above gas mixture, under the indicated reaction conditions, over the active charcoal until the latter is saturated, ie. until cobalt carbonyl and cobalt hydrocarbonyl are determined analytically at the outlet.

The resulting aqueous solution containing cobalt hydrocarbonyl, unconverted cobalt salt and liberated acid is extracted, advantageously together with the unconsumed mixture of carbon monoxide and hydrogen, and advantageously without letting-down, with butadiene or with butadiene-containing hydrocarbon mixtures. The extraction can be carried out using the total amount of butadiene required for the carbonylation or only a fraction of this amount, for example from 5 to 30 moles of butadiene per gram atom of cobalt to be extracted. The extraction is advantageously carried out in counter-current or co-current, for example in columns or static mixers at from 20° to 100° C. and under from 5 to 300 bar. The mixture is then separated into an aqueous phase and an organic phase and at the same time the mixture of carbon monoxide and hydrogen which is also used is separated off as the gas phase. The cobalt content of the organic phase is in general from 1 to 5% by weight. This organic phase is used as the catalyst solution for the carbonylation. The aqueous phase which is separated off still contains up to 1% by weight of cobalt in the form of the cobalt salt used and also contains up to 4% by weight of free acid, corresponding to the cobalt salt used. This aqueous solution is advantageously employed to recover the cobalt catalyst from the reaction mixture, as is described below.

In addition to unconverted butadiene, possibly together with other hydrocarbons, the reaction mixture obtained in the first stage (carbonylation) contains tertiary nitrogen bases, cobalt carbonyl catalyst, unconverted alkanols, the alkyl pentenoates produced as useful products, and also by-products such as valerates, vinylcyclohexene, butenyl and butyl ketoesters and polymers of butadiene.

According to the invention, tertiary nitrogen bases, excess alkanols and any unconverted hydrocarbons which may be present are separated off, advantageously quantitatively, from the abovementioned reaction mixture, for example by distillation. An essential characteristic feature of the invention is that the reaction mixture is treated, before or during the separation, i.e distillation, with gases containing molecular oxygen. Preferably, 1-10 times the equivalent amount of molecular oxygen per gram atom of cobalt is used. Gases containing molecular oxygen have, for example, an oxygen content of from 0.5 to 30% by volume. For industrial purposes, air has proved particularly suitable. Advantageously, the treatment with gases containing molecular oxygen is carried out at from 80° to 100° C. By this means it is possible to remove the tertiary nitrogen bases quantitatively from the reaction mixture without decomposing the catalyst to metallic cobalt. If the treatment with gases containing molecular oxygen is carried out during the distillation, these gases are advantageously fed in at the bottom of the column. If the treatment is carried out prior to the distillation, the reaction mixture is treated, for example, for from 0.01 to 5 minutes with gases containing molecular oxygen, whilst mixing thoroughly.

The bottom product thus obtained from the distillation contains alkyl pentenoates, cobalt catalyst and higher-boiling by-products and is used for the hydroformylation in the second stage. In this stage, the alkyl pentenoate is reacted at from 100° to 160° C. and under from 100 to 300 bar with carbon monoxide and hydrogen in the presence of the cobalt catalyst remaining in the reaction mixture. The reaction is advantageously carried out at from 110° to 130° C. and from 50 to 250 bar. The composition and amount of the mixture of carbon monoxide and hydrogen correspond to that described above for the preparation of the catalyst. Furthermore, it has proved advantageous to carry out the hydroformylation in the presence of solvents. Examples of suitable solvents are aromatics, eg. benzene and toluene, ethers, eg. tetrahydrofuran, and carboxylic acid esters, eg. valerates, butyrates or acetates.

After letting-down, the resulting reaction mixture is advantageously treated with oxidizing agents, such as hydrogen peroxide or gases containing molecular oxygen, especially air, advantageously in an amount of from 2 to 10 oxidation equivalents per mole of cobalt compound. The treatment is advantageously carried out using the acidic aqueous solution obtained from the preparation of the cobalt catalyst. Suitable fatty acids can also be added to the solution, to keep the cobalt in solution. To ensure that the cobalt solution is not obtained in too high a dilution, it is advantageous to recycle the aqueous cobalt-containing solution into the treatment chamber and to separate off only a small part-stream of the amount fed in. The oxidation is advantageously effected at from 80° to 160° C., especially from 100° to 130° C. The reaction is complete after only a few seconds and frequently within fractions of a second, depending on the degree of mixing. To ensure thorough mixing it is advisable to feed the finely dispersed reaction mixture into the aqueous acidic solution whilst at the same time feeding in the oxidizing agent.

After the treatment, the mixture is separated, for example by decanting, into an organic phase and an aqueous phase. Cobalt salts and, if desired, the aqueous phase containing free acid are re-used for preparation of the catalyst. Fractional distillation of the organic phase gives the solvent and unconverted pentenoate, which can be recycled to the hydroformylation, and also a mixture of formylvalerates. The mixture of esters can be used for the preparation of diols and plasticizers. ω-Formylvalerate is obtainable from the mixture of formylvalerates by fractional distillation and can be used for the preparation of ε-caprolactone, ε-caprolactam, hexanediol and adipic acid.

The process according to the invention is illustrated by the following Example.

EXAMPLE

A high-pressure tube filled with 800 ml of active charcoal is fed with 400 ml per hour of an aqueous cobalt acetate solution having a cobalt content of 2%, and 110 liters (S.T.P.) per hour of an equimolar mixture of carbon monoxide and hydrogen are also introduced, a temperature of 140° C. and a pressure of 300 bar being maintained throughout. The solution withdrawn from the other section of the tube contains 0.5% by weight of $Co^{2+}$ and 1.5% by weight of Co in the form of cobalt hydrocarbonyl, and the corresponding amount of acetic acid. After letting-down to 20 bars, this solution is thoroughly mixed at 40° C. with 540 ml of a C₄ cut containing 40% by weight of butadiene (2.52 moles). After phase separation, the C₄ cut contains 6 g of cobalt in the form of cobalt carbonyl compounds, and this cut is then fed to a high-pressure vessel of 2.5 liters capacity into which, per hour, 200 ml (2.52 moles) of pyridine, 200 ml (5.04 mols) of methanol and 120 liters (S.T.P.) of carbon monoxide are also fed. Carbonylation proceeds at 135° C. and under 900 bar. The product withdrawn at the top of the high-pressure vessel is let down and, in addition to excess carbon monoxide, excess C₄ hydrocarbons, which are virtually butadiene-free, are separated off as gases. The pyridine and the unconverted methanol are then distilled off (300 ml of distillate/hour) from the discharged reaction product, 50 liters (S.T.P.) per hour of air being fed to the bottom of the column. The bottom product from the distillation contains 6 g of cobalt catalyst (calculated as cobalt) and 258 g (2.27 moles) of pentenoate; after adding 258 g of ethyl butyrate as the diluent, the product is fed continuously, together with 100 liters (S.T.P.) of synthesis gas (CO:H₂=1:1) to the bottom of a high-pressure vessel of 2.4 liters capacity. The hydroformylation is carried out at 120° C. and under 200 bar. Analysis, by gas chromatography, of the resulting discharged material (580 g/hour) shows that 2% of the pentenoates fed in have been converted to valerates, 93% to formylvalerates, containing 70% of the normal ester, and 5% to high-boiling products (aldolization products).

The discharged reaction product is mixed thoroughly at 100° C., in a tube packed with Raschig rings, with 400 ml/hour of the aqueous solution, containing acetic acid, obtained in the extraction stage, whilst passing 300 liters (S.T.P.)/hour of air through the mixture. After separation, 400 ml of aqueous 2% strength cobalt acetate solution are obtained and are recycled to stage (a) for pre-carbonylation. Fractional distillation of the organic phase gives butyrates (about 250 g), valerates (about 5 g), formylvalerates (about 300 g) and high-boiling products (about 20 g).

We claim:

1. A process for the preparation of an alkyl formylvalerate which comprises:

reacting butadiene or a butadiene-containing hydrocarbon mixture, in a first stage, with carbon monoxide and an alkanol in the presence of a cobalt carbonyl complex catalyst and in the presence of from 0.5 to 2 moles of a tertiary nitrogen base having a $pK_a$ of from 3 to 11 at a temperature of from 80° to 150° C. and a pressure from 300 to 2000 bar;

distilling off from the reaction mixture obtained in the first stage the tertiary nitrogen base, excess alkanol and any unconverted hydrocarbons;

contacting the reaction mixture prior to or during said distillation step with molecular oxygen, and, thereafter in a second stage reacting the alkyl pentenoate formed in the first stage with carbon monoxide and hydrogen in the presence of the residual cobalt catalyst from the first stage at a temperature of from 100° to 160° C. and a pressure of from 100 to 300 bar.

2. The process of claim 1, wherein the treatment with gas containing molecular oxygen is carried out at from 50° to 120° C.

3. The process of claim 1, wherein 1–10 oxidation equivalents of molecular oxygen per gram atom of cobalt are used.

* * * * *